(12) United States Patent
Cane' et al.

(10) Patent No.: US 11,260,175 B2
(45) Date of Patent: Mar. 1, 2022

(54) DEVICE FOR FILLING AND PRIMING SYRINGES

(71) Applicant: CANE' S.P.A., Rivoli (IT)

(72) Inventors: Mario Cane', Rivoli (IT); Paolo Cane', Rivoli (IT); Claudio Cane', Rivoli (IT)

(73) Assignee: Cane' S.p.A., Rivoli (IT)

( * ) Notice: Subject to any disclaimer, the term of this patent is extended or adjusted under 35 U.S.C. 154(b) by 417 days.

(21) Appl. No.: 16/339,442

(22) PCT Filed: Oct. 2, 2017

(86) PCT No.: PCT/IB2017/056065
§ 371 (c)(1),
(2) Date: Apr. 4, 2019

(87) PCT Pub. No.: WO2018/065880
PCT Pub. Date: Apr. 12, 2018

(65) Prior Publication Data
US 2020/0046899 A1    Feb. 13, 2020

(30) Foreign Application Priority Data

Oct. 5, 2016  (IT) ......................... 102016000100047
Oct. 5, 2016  (IT) ......................... 102016000100057
Feb. 20, 2017 (IT) ......................... 102017000018931

(51) Int. Cl.
*A61M 5/00*     (2006.01)
*A61M 5/178*    (2006.01)
(Continued)

(52) U.S. Cl.
CPC ........ *A61M 5/1782* (2013.01); *A61M 5/2053* (2013.01); *A61M 5/3148* (2013.01);
(Continued)

(58) Field of Classification Search
CPC ............... B65B 3/003; A61M 2207/00; A61M 2207/10; A61M 5/1782; A61M 2005/3114; A61M 2209/045
See application file for complete search history.

(56) References Cited

U.S. PATENT DOCUMENTS 5,176,642 A * 1/1993 Clement ............. A61M 1/0062
                                              604/135
5,887,764 A * 3/1999 Ennis, III ............... B05C 17/015
                                              222/389

(Continued)

FOREIGN PATENT DOCUMENTS

DE     19928845 A1    12/2000

*Primary Examiner* — William R Carpenter
(74) *Attorney, Agent, or Firm* — Howson & Howson LLP

(57) ABSTRACT

A device for filling and priming syringes is provided and comprises a support base, an engagement seat defined on the support base to receive a rear end of a syringe barrel of a syringe provided with a sliding plunger, engaging means defined at the engagement seat to cooperate with the syringe barrel for firmly holding the syringe to the engagement seat, a first vacuum pump or compressor which is provided with a suction opening communicating with the engagement seat to generate an under-pressure in the volume comprised between the plunger and the engagement seat when the syringe is firmly engaged in the engagement seat, and a second vacuum pump or compressor which is provided with a discharge opening communicating with the engagement seat to generate an over-pressure in the volume comprised between the plunger and the engagement seat when the syringe is thinly engaged in the engagement seat.

9 Claims, 3 Drawing Sheets

(51) Int. Cl.
*A61M 5/20* (2006.01)
*A61M 5/31* (2006.01)
*B65B 3/00* (2006.01)
*A61M 5/32* (2006.01)

(52) U.S. Cl.
CPC ..... *B65B 3/003* (2013.01); *A61M 2005/3242* (2013.01); *A61M 2209/045* (2013.01)

(56) References Cited

U.S. PATENT DOCUMENTS

| | | | |
|---|---|---|---|
| 6,082,105 A * | 7/2000 | Miyata | A61M 60/135 |
| | | | 60/410 |
| 6,447,487 B1 | 9/2002 | Cane' | |
| D659,234 S | 5/2012 | Cane' | |
| 9,220,835 B2 | 12/2015 | Cane' | |
| 9,289,549 B2 | 3/2016 | Cane' | |
| 9,463,271 B2 | 10/2016 | Cane' | |
| 2006/0224144 A1* | 10/2006 | Lee | A61M 1/67 |
| | | | 604/542 |
| 2007/0175538 A1 | 8/2007 | Rothbauer et al. | |
| 2008/0169043 A1 | 7/2008 | Osborne et al. | |
| 2014/0150337 A1* | 6/2014 | Montecchio | A01G 7/06 |
| | | | 47/57.5 |
| 2016/0030663 A1* | 2/2016 | Adaniya | A61M 5/16877 |
| | | | 604/28 |
| 2016/0151570 A1* | 6/2016 | Rhinehart | A61M 5/3148 |
| | | | 604/149 |
| 2017/0340810 A1 | 11/2017 | Cane' et al. | |

* cited by examiner

DEVICE FOR FILLING AND PRIMING SYRINGES

TECHNICAL FIELD

The invention concerns a device for filling and priming syringes. More particularly, the invention concerns a filling and priming device adapted to be used for filling syringes of the disposable type and for priming air at the end of filling. The device is intended mainly, though not exclusively, for syringes equipped with a detachable sliding rod, i.e. a sliding rod that can be detached from the plunger.

PRIOR ART

The use of syringes for infusing substances, usually drugs, into the body of a living being has been known for a long time. These syringes include a syringe cylindrical barrel open at both ends and having a sliding plunger to cause suction and infusion of the liquid substance through the front opening. The rear opening is provided for inserting the plunger and for controlling the to and fro movement of the plunger by means of a rod that can be actuated either manually or by means of a motor-driven device. The syringe barrel is further usually provided with coplanar and diametrically opposite lugs extending radially at the outside, at the base or rear end of the syringe.

According to prior art, the syringe is filled by axially moving the sliding plunger of the syringe within the syringe barrel in order to generate an under-pressure by which the liquid substance is sucked through the front opening of the syringe.

Therapies involving use of a syringe for infusing substances into a patient's body have become widespread also because of the adoption of programmable electromechanical infusion devices. Such devices are capable of exerting a strong thrust onto the plunger of a syringe and therefore allow use even of large-size syringes. Some known models of infusion devices have a slider acting onto the rod of the syringe, whereas some other known models of infusion devices have an extendable rod equipped with a pusher head acting directly onto the plunger of the syringe without syringe rod. Such known devices require preparation of the syringes, usually disposable syringes, which must be filled with the substance to be infused. Filling can be carried out by the patient himself/herself and may require some effort, especially when the syringes are of a large size and/or the drug is particularly dense. Consequently, particularly within the medical field, the need is felt to provide devices facilitating filling of the syringes, so as to allow this operation to be carried out in an effortless manner also by weak patients or patients with joint problems.

An example for devices of the aforesaid kind, allowing effortless filling of a syringe, is disclosed in US2016/151570 (A1).

The known devices, while substantially eliminating the effort that the user should make in order to fill a syringe, are, however, not free from drawbacks. For example, one drawback lies in the fact that, in order to prevent infusion of air into the body of the living being, as a rule the syringe must not be filled with air, not even with small amounts of air, but it must be filled solely with the liquid substance that is then to be infused into the body of a living being. As a matter of fact, suction of air into the syringe during the filling step inevitably requires the plunger to be subsequently slid manually forwards in order to evacuate the air trapped within the syringe.

One of the main objects of the present invention is therefore to effectively solve the problem of how to fill a syringe in an effortless manner and without incurring the drawbacks of prior art approaches and how to allow priming of the air that may be present within the syringe at the end of the suction step. Another object of the invention is to provide a device for filling a disposable syringe, preferably provided with detachable rod, in a simple and reliable manner. A further object of the invention is to provide a device of the aforementioned type which can be used for syringes of different sizes and capacities and is therefore more versatile than known devices. A not least object of the invention is to provide a device for filling syringes that can be manufactured cost-efficiently on a large scale and is therefore suitable for industrial production.

These and other objects are achieved by the device for filling syringes as claimed in the appended claims.

DISCLOSURE OF THE INVENTION

The device for filling and priming syringes according to the invention is capable of causing a liquid, for instance a drug, to be filled into a syringe having a syringe barrel, usually made of plastic material, and a plunger, usually made of rubber, axially sliding within the syringe barrel. In addition, the device according to the invention is capable of evacuating unwanted air that may have been introduced into the syringe during the filling step.

The device according to the invention substantially comprises means adapted to generate, upstream of the plunger, i.e. between the plunger and the rear base of the syringe, an under-pressure relative to the outer environment, so as to cause withdrawal of the plunger towards the rear end of the syringe and consequent filling of the syringe with a liquid. In addition, still according to the invention, the device comprises means adapted to generate, upstream of the plunger, an over-pressure relative to the outer environment, so as to cause advancing of the plunger towards the front end of the syringe and consequent priming of the air that might have entered during the filling step.

In a preferred embodiment of the invention, the device comprises a support base on which an engagement seat is defined in order to receive the rear end of the syringe barrel of a syringe provided with a sliding plunger. At the engagement seat there are preferably defined engaging means adapted to cooperate with the syringe barrel for firmly holding the syringe associated to the engagement seat and for providing the required tight-sealing within the syringe barrel, upstream of the plunger.

According to the invention, the means for causing suction of liquid through the front end of the syringe comprise a first vacuum pump or compressor. Such vacuum pump or compressor is provided with a suction opening communicating with the engagement seat and is adapted to generate an under-pressure in the volume comprised within the sliding plunger of the syringe and the engagement seat when the syringe is firmly engaged in the engagement seat, i.e. upstream of the plunger.

Still according to the invention, the means for generating an over-pressure upstream of the syringe plunger comprise a second vacuum pump or compressor. Said second pump is provided with a discharge opening communicating with the engagement seat and is adapted to generate an over-pressure in the volume comprised between the syringe plunger and the engagement seat when the syringe is firmly engaged in the engagement seat, i.e. upstream of the plunger.

In a preferred embodiment of the invention, the method for operating the device comprises a first step in which, upstream of the plunger, an under-pressure relative to the outer environment is generated so as to cause withdrawal of the plunger towards the rear end of the syringe and consequent filling of the syringe with a liquid. The liquid is sucked into the syringe through the front opening and usually comes from a vial or the like.

In addition, still according to the invention, a second step is provided in which, upstream of the plunger, an over-pressure relative to the outer environment is generated so as to cause advancing of the plunger towards the front end of the syringe and consequent priming of the air that might have entered during the filling step and might have accumulated downstream of the plunger.

Preferably, the device provides that closing of the suction opening of the second vacuum pump takes place in the first step in which an under-pressure is generated, and that closing of the discharge opening of the first vacuum pump takes place in the second step in which an over-pressure is generated.

According to the invention, the device comprises a first electrically operated valve associated to the discharge or evacuation opening of the first pump. Said first electrically operated valve may preferably be of the normally open type or normally closed type, i.e. capable of allowing priming of air from said discharge opening when said valve is not excited or is excited, respectively. Still according to the invention, the device comprises a second electrically operated valve associated to the suction opening of the second pump. Said second electrically operated valve may be of the normally open type or normally closed type, i.e. capable of allowing suction of air from said suction opening when said valve is not excited or is excited, respectively.

Advantageously, according to the invention, the first pump, the second pump, the first electrically operated valve and the second electrically operated valve are connected to a single electric circuit provided with a battery power supply and a momentary switch with three positions. A first momentary position of the switch controls operation of the first pump and excitation of the corresponding electrically operated valve which has to be brought to the opening or closing position. A second momentary position of the switch controls operation of the second pump and excitation of the corresponding electrically operated valve which has to be brought to the opening or closing position. A neutral position of the switch, in which the pumps are not powered and the valves are not excited, is taken when none of the momentary positions is selected.

Advantageously, according to the invention, the suction opening of the first pump and the discharge opening of the second pump preferably communicate with a "T"-shaped duct communicating with the engagement seat.

The engagement seat preferably comprises a sealing gasket adapted to cooperate with the syringe barrel of the syringe engaged in the engagement seat and to guarantee the tight-sealing required for enabling generation of an under-pressure or over-pressure in the volume comprised between the plunger of the syringe and the engagement seat when the syringe is firmly engaged in the engagement seat.

According to a preferred embodiment of the invention, said sealing gasket cooperates with the inner walls of the syringe barrel radially relative to the longitudinal axis of the syringe. Alternatively, in other embodiments, for instance when the syringe is provided with a bayonet lock provided within the syringe barrel, the gasket cooperates radially with the outer walls of the syringe barrel or axially with the base of the syringe.

According to a preferred embodiment of the invention, the engagement seat comprises a projection extending axially in the engagement seat.

Advantageously, the device according to the invention can be used for several purposes, especially in the medical field. The device according to the invention can mainly be used advantageously for transferring the liquid contained in a container, for example a vial, into a syringe. In addition, the device can be used to suck liquids from the human body in case of withdrawals, or to remove unwanted liquids formed in the human body, for example in the knee joints.

BRIEF DESCRIPTIONS OF THE FIGURES

Some preferred embodiments of the invention will be described by way of non-limiting examples with reference to the annexed figures, in which.

DESCRIPTION OF SOME PREFERRED EMBODIMENTS

Figure 1:
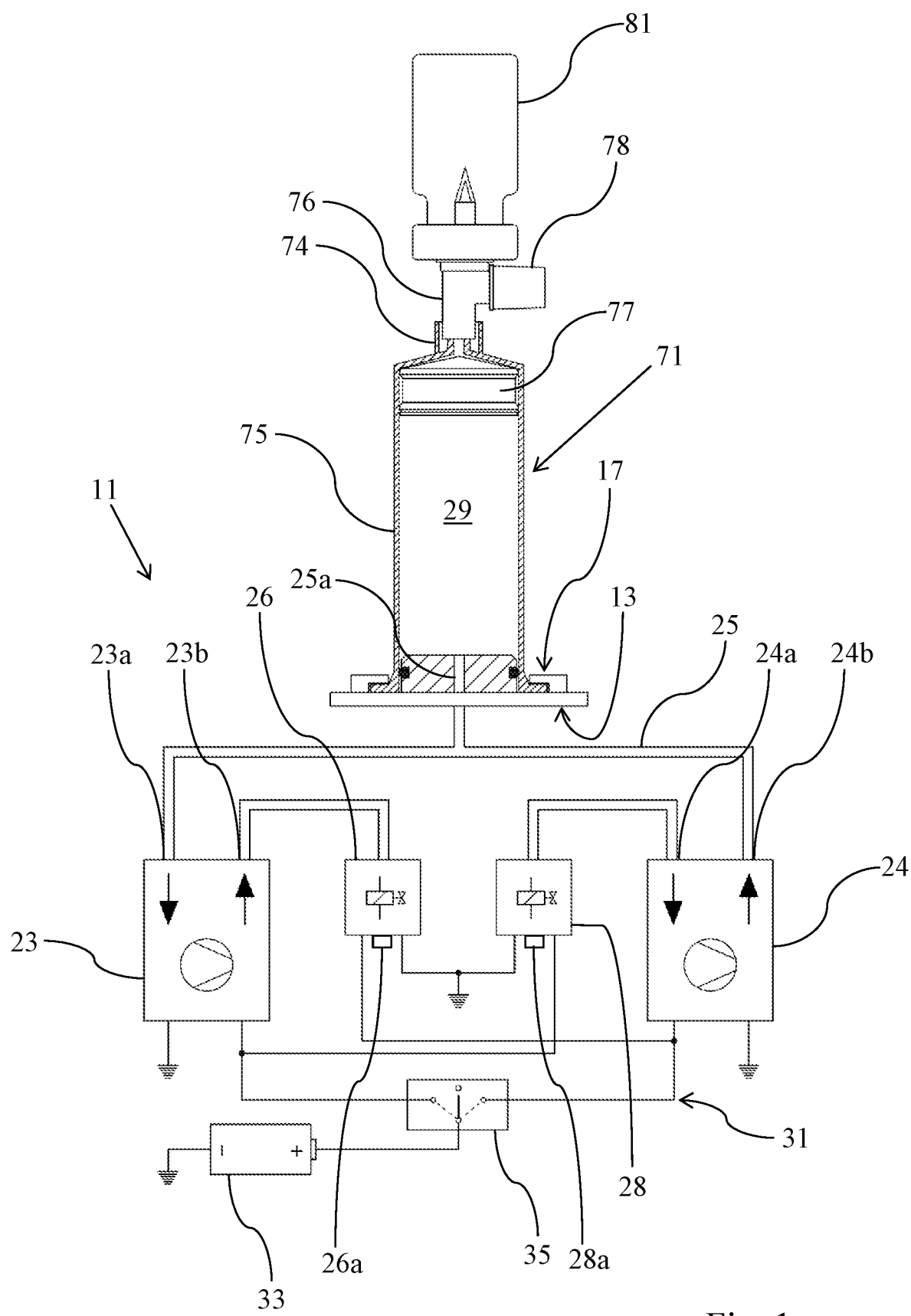
FIG. 1 shows a layout of the device for filling and priming syringes according to a preferred embodiment of the invention, the syringe being shown in a first configuration.
Figure 2:
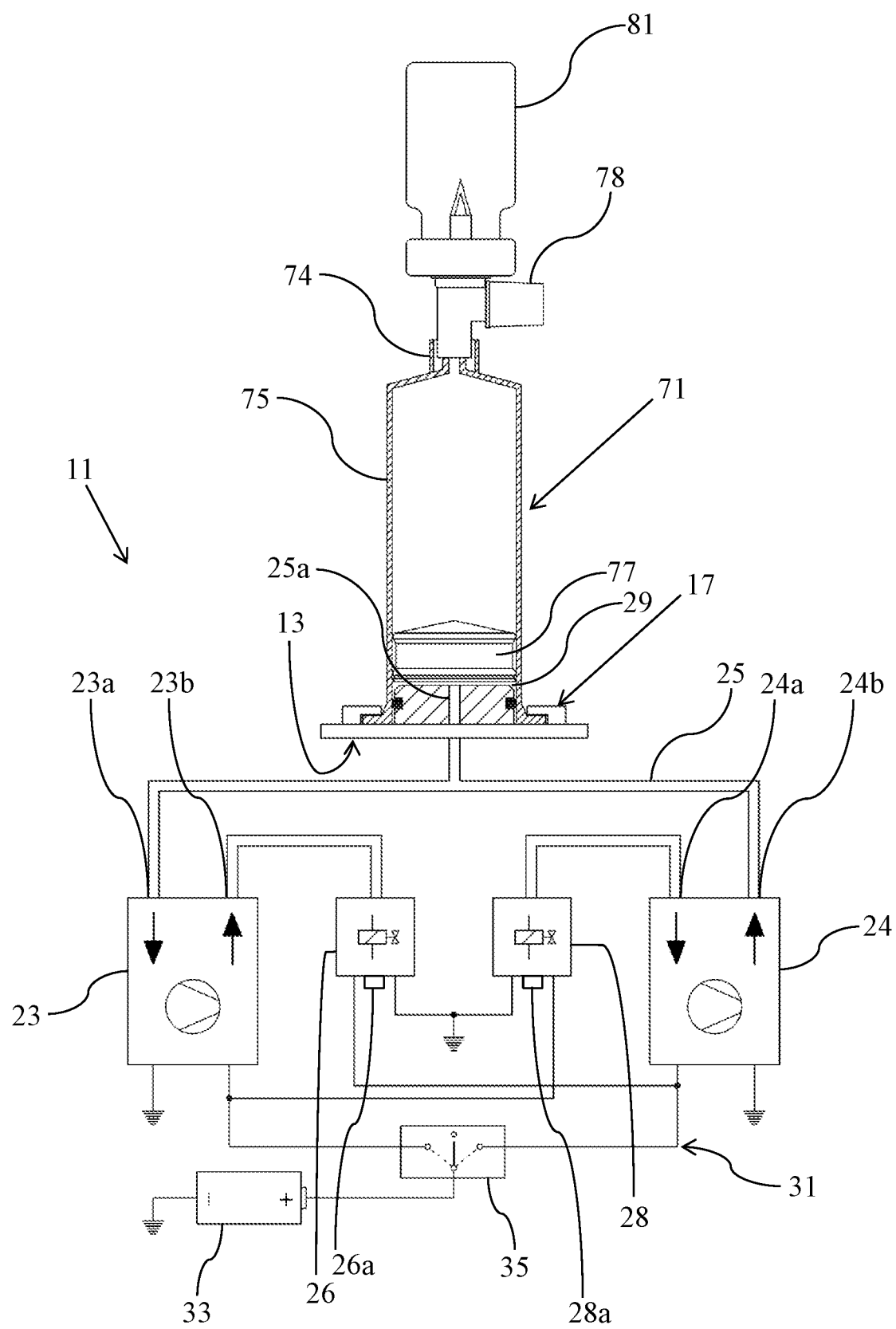
FIG. 2 shows a layout of the device of FIG. 1, the syringe being shown in a second configuration.
Figure 3:
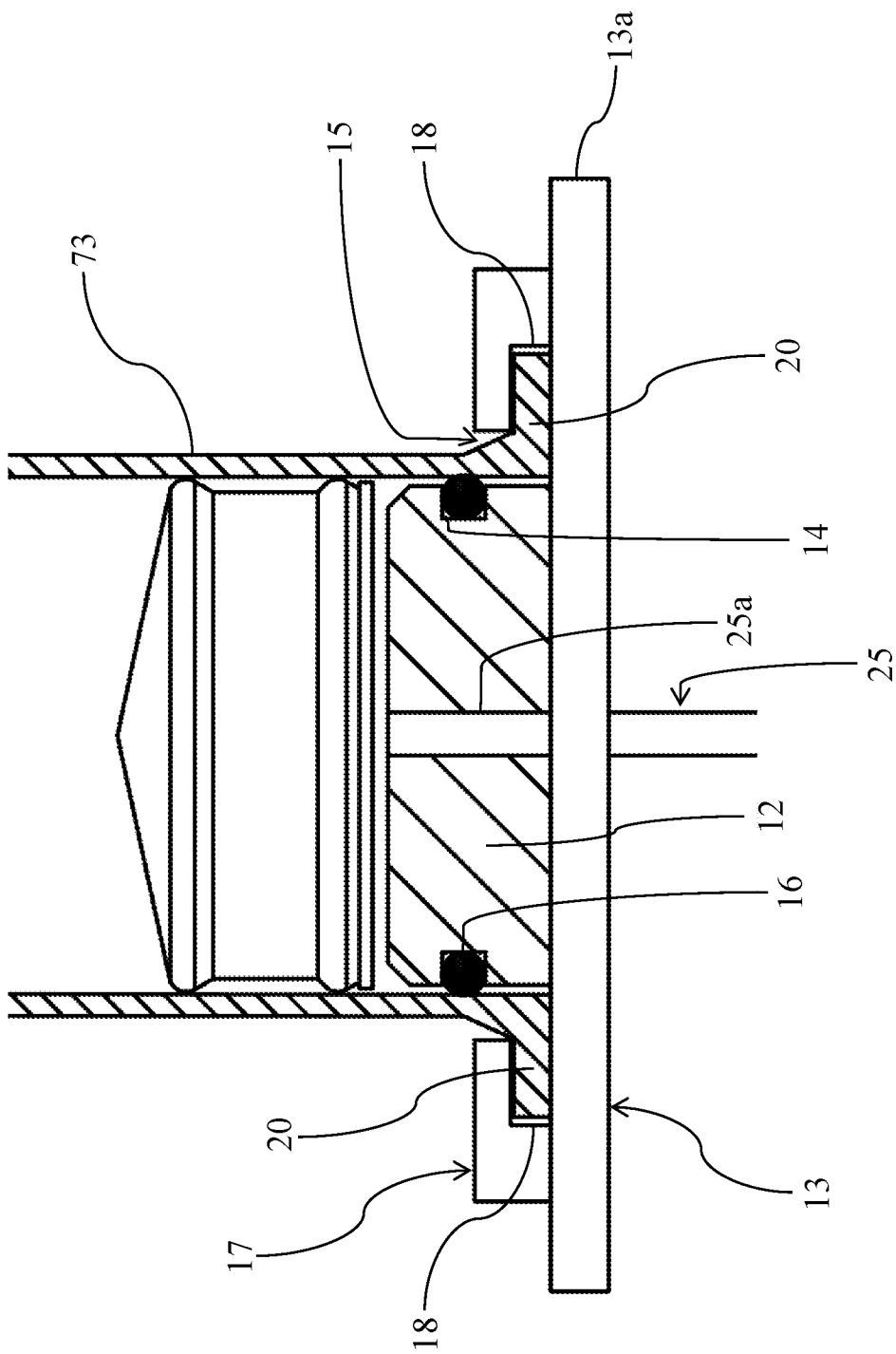
FIG. 3 is an enlarged view of a detail of the filling device of FIG. 1, the syringe being shown in a second configuration.

Referring to the annexed figures, a device 11 for filling syringes is shown, obtained in accordance with a preferred embodiment of the invention. The device 11 comprises a support base 13 on which an engagement seat 15 is defined in order to receive the rear end 73 of the syringe barrel 75 of a syringe 71. The syringe 71 may preferably be of the disposable type, made of a plastic material commonly used in the medical field. The support base 13 of the device 11 preferably comprises a plate 13*a*. The plate 13*a* may be made, for instance, as a ferrule and may be formed as a single piece with a casing enclosing the components of the device 11, or the plate 13*a* can be detachable relative to said casing. The plate 13*a* may further have, for instance, a circular or rectangular shape and close the first end of a hollow cylindrical or prismatic casing receiving the components of the device 11, which components will be described below.

Engaging means 17 are defined at the engagement seat 15 and adapted to cooperate with the syringe barrel 75 for firmly holding the syringe 71, and more particularly the rear end 73, associated to the engagement seat 15. Said engaging means 17 comprise, in the illustrated embodiment, a pair of diametrically opposite grooves 18 which define the female part of a corresponding bayonet lock for the lugs 20 extending radially at the rear end 73 of the syringe barrel 75 of the syringe 71.

According to this embodiment of the invention, the support base 13 further comprises a cylindrical projection 12 extending axially in the engagement seat 15, preferably centrally of said engagement seat. The projection 12 may be made integral with the base 13 or as a separate element connectable, for example by interlocking, to the base 13. In case of a detachable projection 12 it will also be possible to provide devices 11 equipped with a set of projections 12 having different lengths, in order to adapt to different kinds of syringes and volumes of liquid to be introduced.

The projection 12 is provided with an annular groove 14 arranged in a plane substantially parallel to the plane of the base 13. The annular groove 14 accommodates a sealing gasket 16 or O-ring. The gasket 16 may be made of rubber or similar material and has the purpose of forming a tight sealing with the inner surface of the syringe body 75. In this embodiment, the sealing gasket 16 cooperates with the inner walls of the syringe body 75 radially relative to the longitudinal axis of the syringe 71.

According to the invention, the device 11 comprises a pair of vacuum pumps or compressors 23,24. The pumps 23,24 are provided with respective suction openings 23a,24a and discharge or evacuation openings 23b,24b. Still according to the inventions, and for the reasons that will become apparent from the following description, the suction opening 23a of the first pump 23 and the discharge opening 24b of the second pump 24 communicate with the engagement seat 15 through a "T"-shaped duct 25. A portion 25a of the duct 25 extends through the plate 13a and the projection 12 if present, and is in communication with the engagement seat 15. Said duct 25 allows the first pump 23, when started, to evacuate the volume 29 defined upstream of the plunger 77 of the syringe 71, i.e. the volume comprised between the plunger 77 of the syringe 71 and the engagement seat 15. The under-pressure established in the volume 29 as a consequence of evacuation of the air contained therein causes withdrawal of the plunger 77 towards the rear end 73 of the syringe 71. In addition, said duct 25 also allows the second pump 24, when started, to increase the pressure within said volume 29 upstream of the plunger 77, thus causing advancing of the plunger 77 towards the front end 74 of the syringe 71. The first pump 23 is preferably adapted to evacuate into the atmosphere, through an outlet opening 23b provided with an electrically operated valve 26 communicating with the atmosphere through an opening 26a, the air sucked through the duct 25. The second pump 24 is preferably adapted to introduce into the duct 25 the air sucked through the inlet opening 24a provided with an electronically operated valve 28 communicating with the atmosphere through an opening 28a.

The pumps 23,24 and the electrically operated valves 26,28 are connected to the electric circuit 31 provided with a battery power supply 33. Said electric circuit 31 further includes a switch 35, preferably a switch of the momentary type with three positions, for controlling operation of the pumps 23,24 and the electrically operated valves 26,28.

According to prior art, the front end 74 of the syringe 71 is provided with an opening for the inlet and outlet of the liquid, typically a drug. This opening is usually provided with a luer-lock connection, which can be used to connect a vial 81 from which the liquid is sucked into the syringe 71. According to prior art, between the luer-lock connection and the vial 81 there is usually provided a "T"-shaped joint 76 having a ventilation filter 78 through which inlet of a certain amount of air is allowed, which promotes outlet of the liquid from the vial 81 during suction into the syringe 71.

Operation of the device for filling and priming syringes according to this preferred embodiment of the invention will be described in detail below.

When the syringe 71 is engaged in the engagement seat 15 of the device 11 and the vial 81 is connected to the syringe 71 through the joint 76, the first vacuum pump 23 can be started by bringing the switch 35 to a first momentary position. The under-pressure established in the volume 29 comprised between the plunger 77 of the syringe 71 and the engagement seat 15, causes withdrawal of the plunger 77 towards the engagement seat 15 defined on the support base 13. When the first vacuum pump 23 is started, the plunger 77 preferably lies against the ceiling of the syringe barrel 75, near the opening provided at the front end 74. By virtue of the under-pressure generated by the pump 23 the plunger 77 withdraws until it abuts the projection 12.

In this step of filling of the syringe 71, the first electrically operated valve 26 is in its open configuration, in order to allow evacuation, through the opening 23b, of the air sucked by the pump 23 through the duct 25. On the contrary, still referring to this first step of sucking the drug into the syringe, the second pump 24 remains in the off-state and in addition the second electrically operated valve 28 is in its closed configuration, in order to prevent the pump 23 from sucking air through the suction opening 24a, which is also associated to the "T"-shaped duct 25, of the second pump 24.

Subsequently, when the first pump 23 is stopped, at the end of the filling cycle of the syringe 71, by releasing the momentary switch 35, it is preferable to ventilate the volume 29 in order to restore atmospheric pressure. The vacuum generated within the volume 29 would in fact make it difficult to detach the syringe 71 from the seat 15 and it would further involve the risk that during detachment of the syringe 71 from the seat 15, the plunger 77 withdraws towards the rear end 73 of the syringe 71, thus sucking air into the syringe 71 through the front opening. The step of ventilating the volume 29 is also of advantage in causing precise stop of the plunger 77 which, without ventilation, would tend to withdraw as a consequence of residual under-pressure also after release of the momentary switch 35. This ventilation step can be obtained by activating opening of the second valve 28 at the end of the suction step. If said valve 28 is of the normally open type, ventilation of the volume 29 takes place automatically when the momentary switch 35 is released at the end of the first filling step of the syringe 71, during which said second valve 28 is excited in order to keep it closed. If the valve 28 is of the normally closed type, it will have to be excited over a sufficient time at the end of the filling step, for example by means of a condenser charge.

At the end of the filling cycle and after ventilation, if provided, it may be necessary to evacuate unwanted air introduced into the syringe 71 downstream of the plunger 77 during the step of suction of the liquid drug.

In order to evacuate air from the syringe 71, the vial 81 is preferably detached from the syringe 71 and the second vacuum pump 24 can be started by bringing the switch 35 to a second momentary position. The over-pressure established in the volume 29 comprised between the plunger 77 of the syringe 71 and the engagement seat 15, causes advancing of the plunger 77 towards the front end 74 of the syringe 71.

In this second step of air priming, the second electrically operated valve 28 is in its open configuration, in order to allow suction, through the opening 24a, of the air sucked by the pump 24 and introduced into the duct 25. On the contrary, still referring to this step of priming air from the syringe, the first pump 23 is in its off-state and in addition the first electrically operated valve 26 is in its closed configuration, in order to prevent the second pump 24 from evacuating air through the discharge opening 24b.

Subsequently, when the second pump 24 it stopped at the end of the priming cycle of the syringe 71 by releasing the momentary switch 35, it is preferable to ventilate the volume 29 in order to restore atmospheric pressure. The step of ventilating the volume 29 is of advantage especially in causing precise stop of the plunger 77 which, without ventilation, would tend to advance as a consequence of residual over-pressure also after release of the momentary switch 35.

Optionally, a timer associated to the circuit 31 is provided for limiting operation of the second pump 24 to a time interval T1 and preventing subsequent operation of the pump 24 over a time T2. This measure avoids the risk of an excessive outflow of liquid, caused by a delayed release of the momentary switch 35 by the user, out of the syringe 71 during the priming step. In addition, this measures prevents the user from causing spilling of the drug by his/her repeatedly actuating the momentary switch 35. In a preferred embodiment the time T1 is <1.0 s and the time T2 is >5.0 min.

In a preferred embodiment of the invention, the pumps 23,24 are vacuum pumps substantially identical to each other, with an air flow rate of about 1 liter/minute, a maximum vacuum pressure of about −0.3 bar relative to atmospheric pressure and maximum positive pressure of about 0.8 bar relative to atmospheric pressure.

Advantageously, the electrically operated valve 26 will preferably be of the normally open type and the electrically operated valve 28 of the normally closed type, whereby the two electrically operated valves have to be excited only during the priming step, thus reducing electric power consumption.

The electric circuit 31 may be associated to a programmable unit or CPU in order to control operation of the pumps 23,24 and of the valves 26,28 on the basis of a predetermined program, possibly controlled by signals coming from sensors, such as, for instance, a sensor for detecting the position of the plunger 77, a sensor for detecting the presence of the vial 81, a sensor for detecting the presence of the syringe 71 in the seat 15, a sensor for detecting pressure within the volume 29.

The invention as described and illustrated can be subject to several variants and modifications falling within the same inventive principle.

The invention claimed is:

1. A device (11) for filling and priming syringes (71), the device comprising:
   a support base (13) comprising a plate (13a) and provided on a casing enclosing components of the device (11);
   an engagement seat (15) defined on the support base (13) in order to removably receive a rear end (73) of a syringe barrel (75) of a disposable syringe (71), said syringe (71) being provided with a sliding plunger (77), said barrel (75) being provided with a front end (74) with an opening for inlet and outlet of a drug and having lugs (20) extending radially at the rear end (73) of the barrel (75), and said barrel defining an evacuable volume (29) within the barrel (75) between the plunger (77) of the syringe (71) and the engagement seat (15), said volume (29) being variable based upon spatial separation between the plunger (77) and the engagement seat (15) during operation of the device (11);
   engaging means (17) defined at the engagement seat (15) and adapted to cooperate with the syringe barrel (75) for firmly holding the syringe (71) associated to the engagement seat (15), said engaging means (17) comprising a pair of diametrically opposite grooves (18) which define a female part of a bayonet lock for the lugs (20) extending radially at the rear end (73) of the syringe barrel (75);
   a first vacuum pump or compressor (23) enclosed within said casing and which is provided with a suction opening (23a) communicating with the engagement seat (15) and is adapted to generate an under-pressure in the volume (29) comprised between the plunger (77) of the syringe (71) and the engagement seat (15) when the syringe is firmly engaged in the engagement seat (15); and
   a second vacuum pump or compressor (24) enclosed within said casing and which is provided with a discharge opening (24b) communicating with the engagement seat (15) and is adapted to generate an over-pressure in the volume (29) comprised between the plunger (77) of the syringe (71) and the engagement seat (15) when the syringe is firmly engaged in the engagement seat (15);
   wherein the suction opening (23a) of the first vacuum pump or compressor (23) and the discharge opening (24b) of the second vacuum pump or compressor (24) communicate with a "T"-shaped duct (25) communicating with the engagement seat (15) and wherein a portion (25a) of the duct (25) extends through the plate (13a).

2. The device according to claim 1, further comprising:
   a first electrically operated valve (26) associated to a discharge opening (23b) of the first vacuum pump or compressor (23), said first electrically operated valve (26) being a normally open type valve capable of allowing priming of air from said discharge opening (23b) when said first electrically operated valve is not excited or normally closed type valve capable of allowing priming of air from said discharge opening (23b) when said first electrically operated valve is excited; and
   a second electrically operated valve (28) associated to a suction opening (24a) of the second vacuum pump or compressor (24), said second electrically operated valve (28) being a normally open type valve capable of allowing priming of air from said suction opening (24a) when said second electrically operated valve is not excited or normally closed type valve capable of allowing suction of air from said suction opening (24a) when said second electrically operated valve is excited.

3. The device according to claim 2, wherein the first vacuum pump or compressor (23), the second vacuum pump or compressor (24), the first electrically operated valve (26) and the second electrically operated valve (28) are connected to an electric circuit (31) provided with a battery power supply (33) and a momentary switch (35) with three positions, a first momentary position being adapted to control operation of the first vacuum pump or compressor (23) and a second momentary position being adapted to control operation of the second vacuum pump or compressor (24).

4. The device according to claim 1, wherein the engagement seat (15) comprises a sealing gasket (16) adapted to cooperate with the syringe barrel (75) of the syringe (71) engaged in the engagement seat (15) and to guarantee a tight-sealing required for enabling generation of an under-pressure or over-pressure relative to the outer environment in the volume (29) comprised between the plunger (77) of the syringe (71) and the engagement seat (15) when the syringe is firmly engaged in the engagement seat (15).

5. The device according to claim 4, wherein the sealing gasket (16) cooperates with inner walls of the syringe barrel (75) radially relative to a longitudinal axis of the syringe (71).

6. The device according to claim 4, wherein the engagement seat (15) comprises a projection (12) extending axially in the engagement seat (15).

7. A method for filling and priming a syringe (71) having a syringe barrel (75) and a sliding plunger (77), the method comprising the steps of:
   providing the device (11) according to claim 1;
   generating, upstream of the plunger (77), an under-pressure relative to the outer environment, so as to cause withdrawal of the plunger (77) towards the rear end (73) of the syringe (71) and consequent filling of the syringe (71) with a liquid; and
   generating, upstream of the plunger (77), an over-pressure relative to the outer environment, so as to cause advancing of the plunger (77) towards the front end (74) of the syringe (71) and consequent priming of air that entered the syringe (71) during the filling step.

8. The method according to claim 7, wherein said steps of generating an under-pressure is obtained by the first vacuum pump or compressor (23) and an over-pressure is obtained by the second vacuum pump or compressor (23,24).

9. The method according to claim 8, wherein the step of generating an under-pressure comprises closing a suction opening (24*a*) of the second vacuum pump or compressor (24) and the step of generating an over-pressure comprises closing a discharge opening (23*b*) of the first vacuum pump or compressor (23).

\* \* \* \* \*